US006503908B1

(12) United States Patent
Maw

(10) Patent No.: US 6,503,908 B1
(45) Date of Patent: Jan. 7, 2003

(54) PHARMACEUTICALLY ACTIVE COMPOUNDS

(75) Inventor: Graham Nigel Maw, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/685,160

(22) Filed: Oct. 6, 2000

(30) Foreign Application Priority Data

Oct. 11, 1999 (GB) .............................................. 9924028
Mar. 28, 2000 (GB) .............................................. 0007345

(51) Int. Cl.$^7$ ........................ A61K 31/53; C07D 487/00
(52) U.S. Cl. ....................... 514/243; 544/184
(58) Field of Search ........................... 514/243; 544/184

(56) References Cited

U.S. PATENT DOCUMENTS 6,362,178 B1 * 3/2002 Niewohner et al. ......... 514/218

FOREIGN PATENT DOCUMENTS

| DE | 19827640 | 12/1999 |
|----|----------|---------|
| GB | 2346877 | 8/2000 |
| WO | WO 9924433 | 5/1999 |
| WO | WO 0024745 | 5/2000 |

OTHER PUBLICATIONS

Eur Urol 2000, 37 (suppl 2), p. 81.

Berge et al., J. Pharm, Sci., 66, 1–19, 1977.

* cited by examiner

Primary Examiner—Mukund J. Shah
Assistant Examiner—Tamthom N. Truong
(74) Attorney, Agent, or Firm—Peter C. Richardson; Gregg C. Benson; James T. Jones

(57) ABSTRACT

There is provided compounds of formula I,

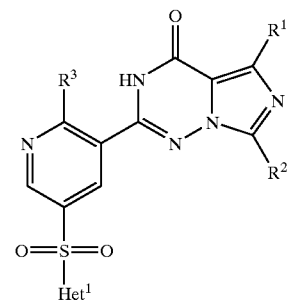

wherein $R^1$, $R^2$, $R^3$ and $Het^1$ have meanings given in the description, which are useful in the curative and prophylactic treatment of medical conditions for which inhibition of a cyclic guanosine 3',5'-monophosphate phosphodiesterase (e.g. cGMP PDE5) is desired.

16 Claims, No Drawings

PHARMACEUTICALLY ACTIVE COMPOUNDS

FIELD OF THE INVENTION

This invention relates to pharmaceutically useful compounds, in particular compounds which are useful in the inhibition of cyclic guanosine 3',5'-monophosphate phosphodiesterases (cGMP PDEs), such as type 5 cyclic guanosine 3',5'-monophosphate phosphodiesterases (cGMP PDE5). The compounds therefore have utility in a variety of therapeutic areas, including male erectile dysfunction (MED).

PRIOR ART

Certain cGMP PDE-inhibiting 2-phenyl substituted imidazotriazinone derivatives are disclosed in international patent application WO 99/24433.

DISCLOSURE OF THE INVENTION

According to a first aspect of the invention there is provided compounds of formula I,

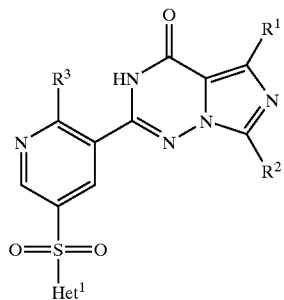

wherein $R^1$ and $R^2$ independently represent phenyl (optionally substituted by one or more substituents selected from halo, —CN, —$CF_3$, —$OCF_3$, $C_{1-4}$ alkoxy or $C_{1-4}$ alkyl (which latter two groups are optionally substituted by $C_{1-4}$ haloalkyl or $C_{1-4}$ haloalkoxy)) or $C_{1-6}$ alkyl optionally interrupted by —O—, —S— and/or —N($R^4$)— and/or optionally substituted and/or terminated by $Het^2$, a N-linked heterocyclic group (selected from piperidinyl and morpholinyl) or phenyl (which latter group is optionally substituted by one or more substituents selected from halo, —CN, —$CF_3$, —$OCF_3$, $C_{1-4}$ alkoxy or $C_{1-4}$ alkyl (which latter two groups are optionally substituted by $C_{1-4}$ haloalkyl or $C_{1-4}$ haloalkoxy));

$R^4$ represents H or $C_{1-4}$ alkyl;

$R^3$ represents $OR^5$ or $N(R^6)R^7$;

$R^5$ represents $C_{3-6}$ cycloalkyl, —($C_{1-4}$ alkylene)-1-piperidinyl, tetrahydrofuranyl, tetrahydropyranyl or $C_{1-6}$ alkyl, which latter group is optionally substituted and/or terminated by one or two substituents selected from $C_{3-5}$ cycloalkyl, —$OR^8$, —$N(R^6)R^7$, phenyl, furanyl and pyridinyl, and which $C_{1-6}$ alkyl group is optionally terminated by a $C_{1-4}$ haloalkyl group;

$R^6$ and $R^7$ independently represent, at each occurrence when used herein, H, $C_{1-4}$ alkyl (optionally substituted by $C_{3-5}$ cycloalkyl or $C_{1-4}$ alkoxy), or $R^6$ and $R^7$, together with the nitrogen atom to which they are attached, form an azetidinyl, pyrrolidinyl, piperidinyl or morpholinyl group;

$R^8$ represents H, $C_{1-4}$ alkyl (which $C_{1-4}$ alkyl group is optionally terminated by a $C_{1-4}$ haloalkyl group) or benzyl;

$Het^1$ represents a 4-$R^9$-1-piperazinyl group optionally substituted with one or two $C_{1-4}$ alkyl groups and optionally in the form of its 4-N-oxide;

$R^9$ represents H, pyridinyl, pyrimidinyl, $C_{3-6}$ alkenyl or $C_{1-4}$ alkyl optionally substituted by one or two substituents selected from —OH, —$N(R^6)R^7$, —C(O)N($R^6$)$R^7$, benzodioxolyl, benzodioxanyl or phenyl (which latter group is optionally substituted by $C_{1-4}$ alkoxy);

$Het^2$ represents a C-linked 6-membered heterocyclic group containing one or two nitrogen atoms, optionally in the form of its mono-N-oxide, or a C-linked 5-membered heterocyclic group containing two or three nitrogen atoms, wherein either of said heterocyclic groups is optionally substituted with $C_{1-4}$ alkyl, $C_{1-4}$ alkoxy or $N(H)R^{10}$; and $R^{10}$ represents H, $C_{1-4}$ alkyl or $C_{1-4}$ alkanoyl;

or a pharmaceutically, or a veterinarily, acceptable derivative thereof;

which compounds are referred to together hereinafter as "the compounds of the invention".

Unless otherwise indicated, each alkyl, alkoxy and alkenyl group identified herein may, when there is a sufficient number of carbon atoms (i.e. three) be linear or branched chain. Alkanoyl groups identified herein may also, when there is a sufficient number of carbon atoms (i.e. four) be linear or branched chain. The term "halo", when used herein, includes fluoro, chloro, bromo and iodo. As used herein, haloalkyl and haloalkoxy groups are preferably —$CF_3$ and —$OCF_3$ respectively.

For the avoidance of doubt, each $R^6$ and $R^7$ group identified herein is independent of other $R^6$ and $R^7$ groups, respectively. For example, when $R^5$ and $R^9$ both represent alkyl substituted by —$N(R^6)R^7$, the two individual —N($R^6$)$R^7$ substituents are independent of one another, and are not necessarily identical (though this possibility is not excluded).

The term "pharmaceutically, or a veterinarily, acceptable derivative" includes salts and solvates. The pharmaceutically or veterinarily acceptable salts of the compounds of the invention which contain a basic centre are, for example, non-toxic acid addition salts formed with inorganic acids such as hydrochloric, hydrobromic, hydroiodic, sulphuric and phosphoric acid, with carboxylic acids or with organosulphonic acids.

Examples include the HCl, HBr, HI, sulphate or bisulphate, nitrate, phosphate or hydrogen phosphate, acetate, benzoate, succinate, saccarate, fumarate, maleate, lactate, citrate, tartrate, gluconate, camsylate, methanesulphonate, ethanesulphonate, benzenesulphonate, p-toluenesulphonate and pamoate salts. Compounds of the invention can also provide pharmaceutically or veterinarily acceptable metal salts, in particular non-toxic alkali and alkaline earth metal salts, with bases. Examples include the sodium, potassium, aluminium, calcium, magnesium, zinc and diethanolamine salts. Pharmaceutically acceptable derivatives also include $C_{1-4}$ alkyl ammonium salts. For a review on suitable pharmaceutical salts see Berge et al, *J. Pharm, Sci.*, 66, 1–19, 1977.

The pharmaceutically acceptable solvates of the compounds of the invention include the hydrates thereof.

Also included within the scope of the compound and various salts of the invention are polymorphs thereof.

Abbreviations are listed at the end of this specification.

Preferred compounds of the invention include those wherein:

R¹ and R² independently represent optionally substituted phenyl or C₁₋₄ alkyl optionally substituted and/or terminated by Het² or optionally substituted phenyl;

R³ represents OR⁵;

R⁵ represents C₁₋₅ alkyl optionally substituted and/or terminated by C₁₋₂ alkoxy;

Het¹ represents a 4-R⁹-1-piperazinyl group;

R⁹ represents C₁₋₄ alkyl;

Het² represents an optionally substituted C-linked 6-membered heterocyclic group containing two, or preferably one, nitrogen atoms.

More preferred compounds of the invention include those wherein:

R¹ and R² independently represent phenyl, methyl, ethyl, propyl, benzyl or pyridylmethyl;

R³ represents ethoxy (optionally substituted or terminated by a methoxy group), propoxy or butoxy;

Het¹ represents 4-ethyl-1-piperazinyl.

The compounds of the invention may exhibit tautomerism. All tautomeric forms of the compounds of formula I and mixtures thereof, are included within the scope of the invention.

A compound of the formula (I) contains one or more asymmetric carbon atoms and therefore exists in two or more stereoisomeric forms. Where a compound of the formula (I) contains an alkenyl or alkenylene group, cis (E) and trans (Z) isomerism may also occur. The present invention includes the individual stereoisomers of the compounds of the formula (I) and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the invention.

Also included within the scope of the invention are radiolabelled derivatives of compounds of formula I which are suitable for biological studies.

Preparation

According to a further aspect of the invention there is provided processes for the preparation of compounds of the invention, as illustrated below.

The following processes are illustrative of the general synthetic procedures which may be adopted in order to obtain the compounds of the invention:

1. Compounds of formula I may be prepared by reaction of a corresponding compound of formula II,

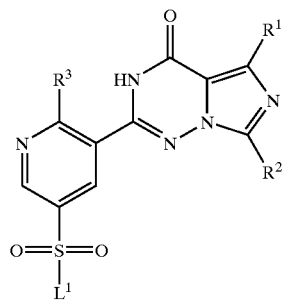

wherein L¹ represents a suitable leaving group (e.g. halo), and R¹, R² and R³ are as hereinbefore defined, with a compound of formula III,

wherein Het¹ is as hereinbefore defined, provided that the 1-N atom of the piperazine is attached to the H-atom.

This reaction is typically performed at between −10° C. and room temperature in the presence of an appropriate solvent (e.g. a C₁₋₃ alcohol, ethyl acetate or dichloromethane), an excess of the compound of formula III and, optionally, another suitable base (e.g. triethylamine or N-ethyldiisopropylamine).

Compounds of formula II may be prepared from a corresponding compound of formula IV,

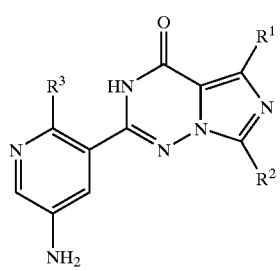

wherein R¹, R² and R³ are as hereinbefore defined, for example using methods known to those skilled in the art for converting an amino group to an SO₂L¹ group, in which L¹ is as hereinbefore defined. For example, compounds of formula II in which L¹ is chloro may be prepared by reacting a corresponding compound of formula IV, at between about −25 and about 0° C., with about a 1.5 to 2-fold excess of sodium nitrite in a mixture of concentrated hydrochloric acid and glacial acetic acid, followed by treatment, at between −30° C. and room temperature, with excess liquid sulfur dioxide and a solution of about a three-fold excess of cupric chloride in aqueous acetic acid.

Compounds of formula IV may be prepared by cyclisation of a corresponding compound of formula V,

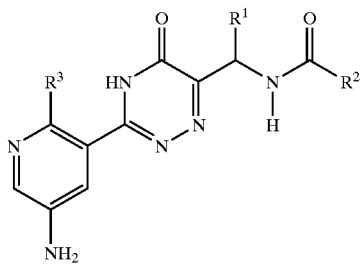

wherein $R^1$, $R^2$ and $R^3$ are as hereinbefore defined, for example under conditions known to those skilled in the art. Such conditions include reaction, at between room and reflux temperature, in the presence of a suitable (Lewis acidic) dehydrating agent (e.g. phosphorous oxychloride) and an appropriate solvent (e.g. 1,2-dichloroethane), or as otherwise described in the prior art.

Compounds of formula V may be prepared by the reduction of a corresponding compound of formula VI,

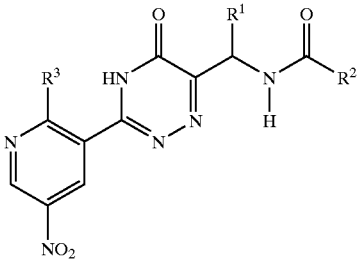

wherein $R^1$, $R^2$ and $R^3$ are as hereinbefore defined, for example by conventional techniques, such as catalytic hydrogenation. Typically, the hydrogenation may be achieved at between 40 and 50° C. using a Raney® nickel catalyst in a suitable solvent (e.g. ethanol) at a hydrogen pressure of between 150 kPa and 500 kPa.

Compounds of formula VI may be prepared by reaction of a corresponding compound of formula VII,

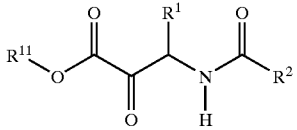

wherein $R^{11}$ represents lower (e.g. $C_{1-6}$) alkyl, and $R^1$ and $R^2$ are as hereinbefore defined, with a compound of formula VIII,

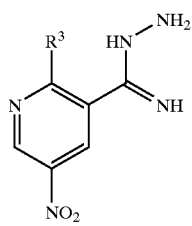

or a suitable acid addition salt thereof (e.g. an hydrogen chloride salt), wherein $R^3$ is as hereinbefore defined, for example under conditions known to those skilled in the art. Such conditions include, for example, reaction at between room and reflux temperature (e.g. 70° C.) in the presence of a suitable solvent (e.g. ethanol, ether, 1,4-dioxane or DMF).

Compounds of formula VII may be prepared via standard techniques, for example by decarboxylation of a corresponding compound of formula IX,

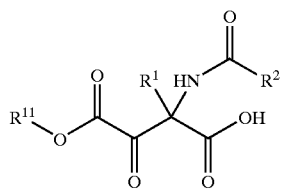

wherein $R^1$, $R^2$ and $R^{11}$ are as hereinbefore defined, for example under conditions known to those skilled in the art. Such conditions include, for example, reaction at elevated temperature (e.g. reflux temperature) in the presence of a suitable solvent (e.g. methanol or ethanol) and optionally in the presence of a suitable base (e.g. sodium hydrogencarbonate).

Compounds of formula IX may be prepared by reaction of a corresponding compound of formula X,

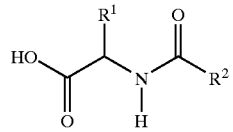

wherein $R^1$ and $R^2$ are as hereinbefore defined, with a compound of formula XI,

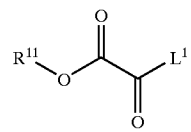

wherein $R^{11}$ and $L^1$ are as hereinbefore defined, for example under conditions known to those skilled in the art. Such conditions include reaction, at between room and reflux temperature, in the presence of a suitable organic solvent (e.g. THF or ether), an appropriate base (e.g. pyridine, sodium hydride, potassium tert-butoxide, lithium diisopropylamide, piperidine or triethylamine) and optionally in the presence of a suitable catalyst (e.g. 4-(dimethylamino)pyridine).

Compounds of formula VII may alternatively be prepared by reaction of a corresponding compound of formula XII,

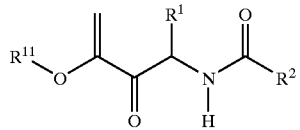

wherein $R^1$, $R^2$ and $R^{11}$ are as hereinbefore defined, with ozone in a stream of oxygen, followed by reduction of the resulting ozonide, for example, for both steps, under conditions known to those skilled in the art. Conditions for the ozonation include, for example, reaction at sub-ambient temperature (e.g. −70° C.) in the presence of a suitable solvent (e.g. dichloromethane). Conditions for reduction of the intermediate ozonide include, for example, reaction at sub-ambient temperature (e.g. −70° C.) with a suitable reducing agent (e.g. dimethyl sulfide), followed by treatment (at the same temperature) with an appropriate base (e.g. pyridine).

Compounds of formula XII may be prepared by reaction of a corresponding compound of formula XIII,

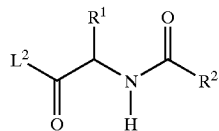

XIII wherein L² represents a suitable leaving group (e.g. —N(CH₃)OCH₃ or halo) and R¹ and R² are as hereinbefore defined, with a compound of formula XIV,

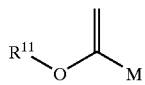

XIV wherein M represents H or a suitable metal-containing moiety (e.g. Na, Li, Mg(II) halide, or a cuprate) and R¹¹ is as hereinbefore defined, for example under conditions known to those skilled in the art. Such conditions include, for example, reaction of a compound of formula XIII at between −80° C. and room temperature in the presence of a suitable solvent (e.g. THF) with a mixture formed by reacting, at sub-ambient temperature (e.g. −78° C.), a compound of formula XIV in which M represents H (e.g. ethyl vinyl ether), a suitable organolithium reagent (e.g. tert-butyllithium), an appropriate solvent (e.g. THF) and, optionally, a source of a suitable metal salt (e.g. MgBr₂ diethyl etherate).

Compounds of formula XIII may be prepared from corresponding compounds of formula X, as hereinbefore defined, under conditions known to those skilled in the art.

Compounds of formula VIII may be prepared via standard techniques, for example by reaction of a corresponding compound of formula XV,

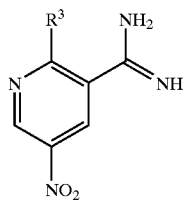

XV or an acid addition salt thereof (e.g. a hydrogen chloride salt), wherein R³ is as hereinbefore defined, with hydrazine, for example under conditions known to those skilled in the art. Such conditions include, for example, reaction at between −10° C. and room temperature in the presence of a suitable solvent (e.g. a lower alkyl (e.g. C₁₋₃) alcohol), or as otherwise described in the prior art.

In a particular embodiment, a compound of formula VIII is formed in situ by reaction at low to ambient temperature (e.g. −10 to 25° C.) of a compound of formula XV with hydrazine hydrate in an alcoholic solution. This is followed by addition of a compound of formula VII, after which the mixture is brought to reflux, eventually yielding a compound of formula VI.

Compounds of formula XV may be prepared from the corresponding cyanopyridine under conditions known to those skilled in the art.

Compounds of formula IV may alternatively be prepared by reduction of a corresponding compound of formula XVI,

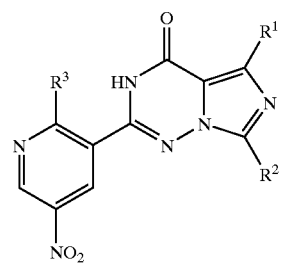

XVI wherein R¹, R² and R³ are as hereinbefore defined, for example under reduction conditions known to those skilled in the art (e.g. as hereinbefore described for the synthesis of compounds of formula V).

Compounds of formula XVI may be prepared in an analogous manner to compounds of formula IV.

Compounds of formula II may alternatively be prepared from a corresponding compound of formula XVII,

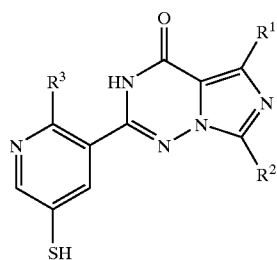

XVII wherein R¹, R² and R³ are as hereinbefore defined, for example by reaction under conditions for conversion of a thiol to an —SO₂L¹ group that are known to those skilled in the art. For example, for compounds of formula II in which L¹ represents halo, the reaction may be carried out at between −10° C. and reflux temperature in the presence of a suitable oxidising agent (e.g. potassium nitrate), an appropriate halogenating agent (e.g. thionyl chloride) and a suitable solvent (e.g. acetonitrile).

Compounds of formula XVII may be prepared by reaction of a corresponding compound of formula XVIII,

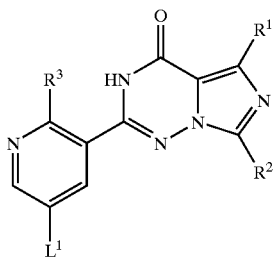

XVIII

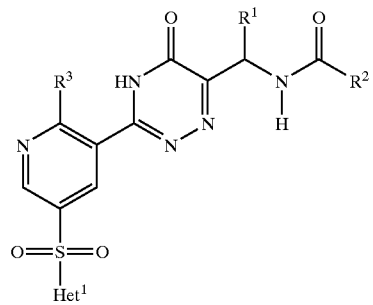

XXI wherein R¹, R², R³ and L¹ are as hereinbefore defined, with a suitable sulfur-delivering reagent. For example, the reaction may be carried out at between room and reflux temperature in the presence of thiourea, an appropriate coupling catalyst (e.g. dichlorobis(triethylphosphine)nickel(II) in combination with a reducing agent such as sodium cyanoborohydride) and a suitable solvent (e.g. N,N-dimethylformamide), followed by cleavage of the resulting thiopseudourea under hydrolytic conditions (e.g. by reaction with a base such as calcium oxide).

Compounds of formula XVIII may be prepared by cyclisation of a corresponding compound of formula XIX,

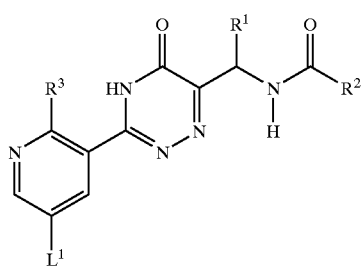

XIX wherein R¹, R², R³ and L¹ are as hereinbefore defined, for example as hereinbefore described for the synthesis of compounds of formula IV.

Compounds of formula XIX may be prepared by reaction of a corresponding compound of formula XX,

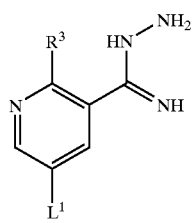

XX wherein R³ and L¹ are as hereinbefore defined, with a compound of formula VII, as hereinbefore defined, for example under conditions described hereinbefore for the synthesis of compounds of formula VI.

2. Compounds of formula I may alternatively be prepared by cyclisation of a corresponding compound of formula XXI, wherein R¹, R², R³ and Het¹ are as hereinbefore defined, for example as hereinbefore described for the synthesis of compounds of formula IV.

Compounds of formula XXI may be prepared by reaction of a corresponding compound of formula XXII,

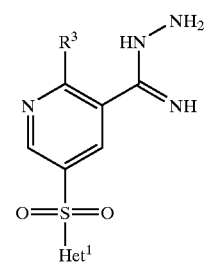

XXII wherein R³ and Het¹ are as hereinbefore defined, with a compound of formula VII, as hereinbefore defined, for example under conditions described hereinbefore for the synthesis of compounds of formula VI.

Compounds of formula XXI may alternatively be prepared by reaction of a corresponding compound of formula XXIII,

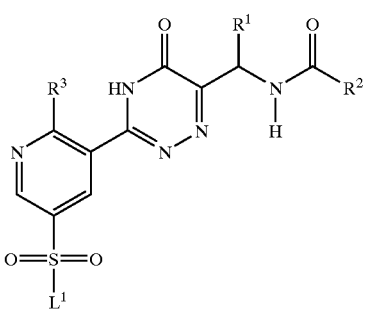

XXIII wherein R¹, R², R³ and L¹ are as hereinbefore defined, with a compound of formula III, as hereinbefore defined, for example under conditions described hereinbefore for the synthesis of compounds of formula I.

Compounds of formula I may alternatively be prepared in accordance, and/or by analogy, with methods described in the prior art for the synthesis of 2-substituted imidazotriazinone ring systems, for example as described in international patent application WO 99/24433 (the disclosure in which document is hereby incorporated by reference).

Compounds of formulae III, X, XI, XIV, XX, XXII, XXIII and derivatives thereof, when not commercially available or not subsequently described, may be obtained either by analogy with the processes described hereinbefore, or by conventional synthetic procedures, in accordance with standard techniques, from readily available starting materials using appropriate reagents and reaction conditions.

Substituents on phenyl and Het ($Het^1$, $Het^2$) groups in the above-mentioned compounds may be introduced, removed and interconverted, using techniques which are well known to those skilled in the art. For example, compounds of formula I as described hereinbefore, in which either $R^1$ or $R^2$ represents $C_{1-6}$ alkyl substituted by an alkylphenyl group, may be prepared by alkylation of a corresponding compound of formula I in which $R^1$ or $R^2$ represents $C_{1-6}$ alkyl substituted by a phenyl group. The reaction may be performed using methods which are well known to those skilled in the art.

The skilled person will also appreciate that various standard substituent or functional group interconversions and transformations within certain compounds of formula I will provide other compounds of formula I. For example, for compounds of formula I in which $R^3$ represents $OR^5$, alkoxide exchange at the 2-position of the pyridin-3-yl substituent. Moreover, certain compounds of formula I for example those in which $Het^1$ represents a 4-$R^9$-1-piperazinyl group, in which $R^9$ does not represent H, may be prepared directly from the corresponding piperazine analogues in which $R^9$ represents H, using standard procedures (e.g. alkylation).

The compounds of the invention may be isolated from their reaction mixtures using conventional techniques.

It will be appreciated by those skilled in the art that, in the course of carrying out the processes described above, the functional groups of intermediate compounds may need to be protected by protecting groups.

Functional groups which it is desirable to protect include hydroxy, amino and carboxylic acid. Suitable protecting groups for hydroxy include trialkylsilyl and diarylalkylsilyl groups (e.g. tert-butydimethylsilyl, tert-butyldiphenylsilyl or trimethylsilyl), tetrahydropyranyl and alkylcarbonyl groups (e.g. methyl- and ethylcarbonyl). Suitable protecting groups for amino include tert-butyloxycarbonyl, 9-fluorenylmethoxycarbonyl or benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art.

The use of protecting groups is fully described in "Protective Groups in Organic Chemistry", edited by JWF McOmie, Plenum Press (1973), and "Protective Groups in Organic Synthesis", $2^{nd}$ edition, T W Greene & P G M Wutz, Wiley-Interscience (1991).

Persons skilled in the art will also appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Pharmaceutically acceptable acid addition salts of the compounds of formula I that contain a basic centre may be prepared in a conventional manner. For example, a solution of the free base may be treated with the appropriate acid, either neat or in a suitable solvent, and the resulting salt may then be isolated either by filtration or by evaporation under vacuum of the reaction solvent. Pharmaceutically acceptable base addition salts can be obtained in an analogous manner by treating a solution of a compound of formula I with the appropriate base. Both types of salt may be formed or interconverted using ion-exchange resin techniques.

The present invention also includes all suitable isotopic variations of a compound of the formula (I) or a pharmaceutically acceptable salt thereof. An isotopic variation of a compound of the formula (I) or a pharmaceutically acceptable salt thereof is defined as one in which at least one atom is replaced by an atom having the same atomic number but an atomic mass different from the atomic mass usually found in nature. Examples of isotopes that can be incorporated into compounds of the formula (I) and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the compounds of the formula (I) and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of formula (I) and pharmaceutically acceptable salts thereof of this invention can generally be prepared by conventional procedures such as by the illustrative methods or by the preparations described in the Examples and Preparations hereafter using appropriate isotopic variations of suitable reagents.

It will be appreciated by those skilled in the art that certain protected derivatives of compounds of formula I which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formula I may act as prodrugs of other compounds of formula I.

All protected derivatives, and prodrugs, of compounds of formula I are included within the scope of the invention.

Medical Use

The compounds of the invention are useful because they possess pharmacological activity in animals, especially mammals, including humans. They are therefore indicated as pharmaceuticals, as well as for use as animal medicaments.

According to a further aspect of the invention there is provided the compounds of the invention for use as pharmaceuticals, and for use as animal medicaments.

In particular, compounds of the invention have been found to be potent and selective inhibitors of cGMP PDEs, such as cGMP PDE5, for example as demonstrated in the tests described below, and are thus useful in the treatment of medical conditions in humans, and in animals, in which cGMP PDEs, such as cGMP PDE5, are indicated, and in which inhibition of cGMP PDEs, such as cGMP PDE5, is desirable.

By the term "treatment", we include both therapeutic (curative), palliative or prophylactic treatment.

Thus, according to a further aspect of the invention there is provided the use of the compounds of the invention in the manufacture of a medicament for the treatment of a medical condition in which a cGMP PDE (e.g. cGMP PDE5) is indicated. There is further provided the use of the compounds of the invention in the manufacture of a medicament for the treatment of a medical condition in which inhibition of a cGMP PDE (e.g. cGMP PDE5) is desirable or required.

The compounds of the invention are thus expected to be useful for the curative, palliative or prophylactic treatment of mammalian sexual disorders. In particular, the compounds are of value in the treatment of mammalian sexual dysfunctions such as male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD) as well as sexual dysfunction due to spinal cord injury but, clearly, will be useful also for treating other medical conditions for which a potent and selective cGMP PDE5 inhibitor is indicated. Such conditions include premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, e.g. post-percutaneous transluminal coronary angioplasty (post-PTCA), peripheral vascular disease, stroke, nitrate induced tolerance, bronchitis, allergic asthma, chronic asthma, allergic rhinitis, glaucoma and diseases characterised by disorders of gut motility, e.g. irritable bowel syndrome (IBS).

Further medical conditions for which a potent and selective cGMP PDE5 inhibitor is indicated, and for which treatment with compounds of the present invention may be useful include pre-eclampsia, Kawasaki's syndrome, nitrate tolerance, multiple sclerosis, diabetic nephropathy, peripheral diabetic neuropathy, Alzheimer's disease, acute respiratory failure, psoriasis, skin necrosis, cancer, metastasis, baldness, nutcracker oesophagus, anal fissure, haemorrhoids and hypoxic vasoconstriction.

Particularly preferred conditions include MED and FSD.

Thus the invention provides a method of treating or preventing a medical condition for which a cGMP PDE5 inhibitor is indicated, in an animal (e.g. a mammal, including a human being), which comprises administering a therapeutically effective amount of a compound of the invention to a mammal in need of such treatment.

Pharmaceutical Preparations

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The compounds of the invention may also be combined with any other drugs useful in the inhibition of cGMP-PDEs, such as cGMP-PDE5.

The compounds of the invention, their pharmaceutically acceptable salts, and pharmaceutically acceptable solvates of either entity can be administered alone but, in human therapy will generally be administered in admixture with a suitable pharmaceutical excipient diluent or carrier selected with regard to the intended route of administration and standard pharmaceutical practice.

For example, the compounds of the invention or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, sustained-, controlled-release or pulsatile delivery applications. The compounds of the invention may also be administered via intracavernosal injection. The compounds of the invention may also be administered via fast dispersing or fast dissolving dosages forms.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e. upon the surface or coating.

Fast dispersing or dissolving dosage formulations (FDDFS) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol.

The compounds of the invention can also be administered parenterally, for example, intracavernosally, intravenously, intra-arterially, intraperitoneally, intrathecally, intraventricularly, intraurethrally intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the invention or salts or solvates thereof will usually be from 10 to 500 mg (in single or divided doses).

Thus, for example, tablets or capsules of the compounds of the invention or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including MED and FSD), compounds of the invention may be taken as a single dose on an "as required" basis (i.e. as needed or desired).

Example Tablet Formulation

In general a tablet formulation could typically contain between about 0.01 mg and 500 mg of a compound according to the present invention (or a salt thereof) whilst tablet fill weights may range from 50 mg to 1000 mg. An example formulation for a 10 mg tablet is illustrated:

| Ingredient | % w/w |
| --- | --- |
| Compound of Example 1 | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™ or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

The compounds of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds of the invention or salts or solvates thereof can be administered in the form of a suppository or pessary, or they may be applied topically in the form of a gel, hydrogel, lotion, solution, cream, ointment or dusting powder. The compounds of the invention or salts or solvates thereof may also be dermally administered. The compounds of the invention or salts or solvates thereof may also be transdermally administered, for example, by the use of a skin patch. They may also be administered by the ocular, pulmonary or rectal routes.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention or salts or solvates thereof can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

Generally, in humans, oral administration of the compounds of the invention is the preferred route, being the most convenient and, for example in MED, avoiding the well-known disadvantages associated with intracavernosal (i.c.) administration. A preferred oral dosing regimen in MED for a typical man is from 25 to 250 mg of compound when required. In circumstances where the recipient suffers from a swallowing disorder or from impairment of drug absorption after oral administration, the drug may be administered parenterally, sublingually or buccally.

For veterinary use, a compound of the invention, or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

Thus, according to a further aspect of the invention there is provided a pharmaceutical formulation including a compound of the invention in admixture with a pharmaceutically or veterinarily acceptable adjuvant, diluent or carrier.

In addition to the fact that compounds of the invention inhibit cyclic guanosine 3',5'-monophosphate phosphodiesterases (cGMP PDEs) and in particular, are potent and selective inhibitors of cGMP PDE5, compounds of the invention may also have the advantage that they may be more efficacious than, be less toxic than, have a broader range of activity than, be more potent than, produce fewer side effects than, be more easily absorbed than, or they may have other useful pharmacological properties over, compounds known in the prior art.

The present invention additionally comprises the combination of a cGMP $PDE_5$ inhibitor, in particular a compound of the general formula (I) with:

(a) one or more naturally occurring or synthetic prostaglandins or esters thereof. Suitable prostaglandins for use herein include compounds such as alprostadil, prostaglandin $E_1$, prostaglandin $E_0$, 13, 14-dihydroprosta glandin $E_1$, prostaglandin $E_2$, eprostinol, natural synthetic and semi-synthetic prostaglandins and derivatives thereof including those described in U.S. Pat. No. 6,037,346 issued on Mar. 14, 2000 and incorporated herein by reference, $PGE_0$, $PGE_1$, $PGA_1$, $PGB_1$, $PGF_1$ α, 19-hydroxy $PGA_1$, 19-hydroxy-$PGB_1$, $PGE_2$, $PGB_2$, 19-hydroxy-$PGA_2$, 19-hydroxy-$PGB_2$, $PGE_3$α, carboprost tromethamine dinoprost, tromethamine, dinoprostone, lipo prost, gemeprost, metenoprost, sulprostune, tiaprost and moxisylate; and/or (b) one or more α-adrenergic receptor antagonist compounds also known as α-adrenoceptors or α-receptors or α-blockers. Suitable compounds for use herein include: the α-adrenergic receptors as described in PCT application WO99/30697 published on Jun. 14, 1998, the disclosures of which relating to α-adrenergic receptors are incorporated herein by reference and include, selective $α_1$-adrenoceptors or $α_2$-adrenoceptors and non-selective adrenoceptors, suitable $α_1$-adrenoceptors include: phentolamine, phentolamine mesylate, trazodone, alfuzosin, indoramin, naftopidil, tamsulosin, dapiprazole, phenoxybenzamine, idazoxan, efaraxan, yohimbine, rauwolfa alkaloids, Recordati 15/2739, SNAP 1069, SNAP 5089, RS17053, SL 89.0591, doxazosin, terazosin, abanoquil and prazosin; $α_2$-blockers from U.S. Pat. No. 6,037,346 [Mar. 14, 2000] dibenarnine, tolazoline, trimazosin and dibenarnine; α-adrenergic receptors as described in U.S. Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference; $α_2$-Adrenoceptors include: clonidine, papaverine, papaverine hydrochloride, optionally in the presence of a cariotonic agent such as pirxamine; and/or (c) one or more NO-donor (NO-agonist) compounds. Suitable NO-donor compounds for use herein include organic nitrates, such as mono-di or tri-nitrates or organic nitrate esters including glyceryl brinitrate (also known as nitroglycerin), isosorbide 5-mononitrate, isosorbide dinitrate, pentaerythritol tetranitrate, erythrityl tetranitrate, sodium nitroprusside (SNP), 3-morpholinosydnonimine molsidomine, S-nitroso-N-acetyl penicilliamine (SNAP) S-nitroso-N-glutathione (SNO-GLU), N-hydroxy-L-arginine, amylnitrate, linsidomine, linsidomine chlorohydrate, (SIN-1) S-nitroso-N-cysteine, diazenium diolates,(NONOates), 1,5-pentanedinitrate, L-arginene, ginseng, zizphi fructus, molsidomine, Re-2047, nitrosylated maxisylyte derivatives such as NMI-678-11 and NMI-937 as described in published PCT application WO 0012075; and/or (d) one or more potassium channel openers. Suitable potassium channel openers for use herein include nicorandil, cromokalim, levcromakalim, lemakalim, pinacidil, cliazoxide, minoxidil, charybdotoxin, glyburide, 4-amini pyridine, $BaCl_2$; and/or (e) one or more dopaminergic agents. Suitable dopaminergic compounds for use herein include $D_2$-agonists such as, pramipexol; apomorphine; and/or (f) one or more vasodilator agents. Suitable vasodilator agents for use herein include nimodepine, pinacidil, cyclandelate, isoxsuprine, chloroprumazine, halo peridol, Rec 15/2739, trazodone, pentoxifylline; and/or (g) one or more thromboxane A2 agonists; and/or (h) one or more CNS active agents; and/or (i) one or more ergot alkoloids; Suitable ergot alkaloids are described in U.S. Pat. No. 6,037,346 issued on Mar, 14, 2000 and include acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride; and/or (k) one or more compounds which modulate the action of atrial natruretic factor (also known as atrial naturetic peptide), such as inhibitors or neutral endopeptidase; and/or (l) one or more compounds which inhibit angiotensin-converting enzyme such as enapril, and combined inhibitors of angiotensin-converting enzyme and neutral endopeptidase such as omapatrilat; and/or (m) one or more angiotensin receptor antagonists such as losartan; and/or (n) one or more substrates for NO-synthase, such as L-arginine; and/or (o) one or more calcium channel blockers such as amlodipine; and/or (p) one or more antagonists of endothelin receptors and inhibitors or endothelin-converting enzyme; and/or (q) one or more cholesterol lowering agents such as statins and fibrates; and/or (r) one or more antiplatelet and antithrombotic agents, e.g. tPA, uPA, warfarin, hirudin and other thrombin inhibitors, heparin, thromboplastin activating factor inhibitors; and/or (s) one or more insulin sensitising agents such as rezulin and hypoglycaemic agents such as glipizide; and/or (t) L-DOPA or carbidopa; and/or (u) one or more acetylcholinesterase inhibitors such as donezipil; and/or (v) one or more steroidal or non-steroidal anti-inflammatory agents.

The biological activities of the compounds of the present invention may be determined by the following test methods.

Biological Tests

Phosphodiesterase (PDE) Inhibitory Activity In vitro PDE inhibitory activities against cyclic guanosine 3',5'-monophosphate (cGMP) and cyclic adenosine 3',5'-monophosphate (cAMP) phosphodiesterases are determined by measurement of their $IC_{50}$ values (the concentration of compound required for 50% inhibition of enzyme activity).

The required PDE enzymes were isolated from a variety of sources, including human corpus cavernosum, human and rabbit platelets, human cardiac ventricle, human skeletal muscle and bovine retina, essentially by the method of W. J. Thompson and M. M. Appleman (*Biochem.*, 1971, 10, 311). In particular, the cGMP-specific PDE (PDE5) and the cGMP-inhibited cAMP PDE (PDE3) were obtained from human corpus cavernosum tissue, human platelets or rabbit platelets; the cGMP-stimulated PDE (PDE2) was obtained from human corpus cavernosum; the calcium/calmodulin (Ca/CAM)-dependent PDE (PDE1) from human cardiac ventricle; the cAMP-specific PDE (PDE4) from human skeletal muscle; and the photoreceptor PDE (PDE6) from bovine retina. Phosphodiesterases 7-11 were generated from full length human recombinant clones transfected into SF9 cells.

Assays were performed either using a modification of the "batch" method of W. J. Thompson et al. (*Biochem.*, 1979, 18, 5228) or using a scintillation proximity assay for the direct detection of AMP/GMP using a modification of the protocol described by Amersham plc under product code TRKQ7090/7100. In summary, the effect of PDE inhibitors was investigated by assaying a fixed amount of enzyme in the presence of varying inhibitor concentrations and low substrate, (cGMP or cAMP in a 3:1 ratio unlabelled to [$^3$H]-labeled at a conc ~1/3 $K_m$) such that $IC_{50} \equiv K_i$. The final assay volume was made up to 100 μl with assay buffer [20 mM Tris-HCl pH 7.4, 5 mM $MgCl_2$, 1 mg/ml bovine serum albumin]. Reactions were initiated with enzyme, incubated for 30–60 min at 30° C. to give <30% substrate turnover and terminated with 50 μl yttrium silicate SPA beads (containing 3 mM of the respective unlabelled cyclic nucleotide for PDEs 9 and 11). Plates were re-sealed and shaken for 20 min, after which the beads were allowed to settle for 30 min in the dark and then counted on a TopCount plate reader (Packard, Meriden, Conn.) Radioactivity units were converted to % activity of an uninhibited control (100%), plotted against inhibitor concentration and inhibitor $IC_{50}$ values obtained using the 'Fit Curve' Microsoft Excel extension. Results from these tests show that the compounds of the present invention are potent and selective inhibitors of cGMP-specific PDE5.

Functional Activity

This was assessed in vitro by determining the capacity of a compound of the invention to enhance sodium nitroprusside-induced relaxation of pre-contracted rabbit corpus cavernosum tissue strips, as described by S. A. Ballard et al. (*Brit. J. Pharmacol.*, 1996, 118(suppl.), abstract 153P).

In vivo Activity

Compounds were screened in anaesthetised dogs to determine their capacity, after i.v. administration, to enhance the pressure rises in the corpora cavernosa of the penis induced by intracavernosal injection of sodium nitroprusside, using a method based on that described by Trigo-Rocha et al. (Neurourol. and Urodyn., 1994, 13, 71).

Safety Profile

Compounds of the invention may be tested at varying i.v and p.o. doses in animals such as mouse and dog, observing for any untoward effects.

The invention is illustrated but in no way limited by the following Preparations and Examples.

Preparation 1

N-Propionylalanine

Trimethylsilyl chloride (52.4 mL, 0.41 mol) was added dropwise to an ice-cooled solution of D,L-alanine (16.71 g, 0.188 mol) and triethylamine (57.5 mL, 0.41 mol) in dichloromethane (190 mL). Once addition was complete, the solution was stirred at room temperature for 1 hour, followed by 1 hour at 40° C. The solution was then cooled to −10° C., propionyl chloride (16.29 mL, 0.188 mol) added dropwise over 15 minutes and, once addition was complete, the reaction was stirred at −10° C. for 2 hours, then 16 hours at room temperature, before cooling in an ice-bath. Water (100 mL) was added, the mixture was stirred for 15 minutes, then the phases separated. The aqueous layer was evaporated under reduced pressure and the residue triturated with acetone. The resulting solid was filtered off, and the filtrate concentrated under reduced pressure, to give an oil. This oil was purified by column chromatography on silica gel using dichloromethane:methanol:0.88 ammonia (89:10:1) as eluant, to give the title compound (20 g; containing 33% triethylamine).

$^1$H NMR (DMSO $d_6$, 300 MHz) L 0.98 (t, 3H), 1.20 (d, 3H), 2.07 (q, 2H), 4.08 (m, 1H), 7.80 (d, 1H), 8.57–9.00 (bs, 1H)

Preparation 2

N-Methoxy-N-methyl-2-(propionylamino) propanamide 1-(3-Dimethylaminopropyl)-3-ethylcarbodiimide hydrochloride (16.2 g, 84.7 mmol) was added to a suspension of the acid from Preparation 1 (14.85 g, 77.0 mmol), triethylamine (27.9 mL, 72.5 mmol), N,O-dimethyl hydroxylamine hydrochloride (7.5 g, 77 mmol) and 1-hydroxybenzotriazole hydrate (12.3 g, 80.85 mmol), in dichloromethane (450 mL) and the reaction stirred at room temperature for 23 hours. The mixture was washed with water (250 mL) and sodium bicarbonate solution (120 mL), dried ($MgSO_4$) and evaporated under reduced pressure. The residual oil was purified by column chromatography on silica gel using dichloromethane:methanol (95:5) as eluant to afford the title compound (8.2 g).

$^1$H NMR ($CDCl_3$, 300 MHz) L 1.17 (t, 3H), 1.34 (d, 3H), 2.22 (q, 2H), 3.20 (s, 3H), 3.79 (s, 3H), 4.98 (m, 1H), 6.23 (bs, 1H)

Preparation 3

N-(3-Ethoxy-1-methyl-2-oxo-3-butenyl) propanamide tert-Butyl lithium (70 mL, 1.7 M in pentane, 119 mmol) was added over 5 minutes to a cooled (−78° C.) solution of ethyl vinyl ether (11.4 mL, 119 mmol) in tetrahydrofuran (160 mL), and the solution allowed to warm to −5° C. over 1 hour. The solution was then re-cooled to −60° C., and magnesium bromide diethyl etherate (30.73 g, 119 mmol) was added portionwise, so as to maintain an internal temperature of less than -50° C. The mixture was then allowed to warm to −5° C., stirred for 30 minutes, and re-cooled to −10° C. A solution of the amide from Preparation 2 (2.8 g, 14.9 mmol) in tetrahydrofuran (20 mL) was added dropwise, and the reaction then stirred at room temperature for 3 hours.

The mixture was poured into 10% aqueous citric acid solution (500 mL) and extracted with ethyl acetate (500 mL). The organic solution was dried (MgSO$_4$) and evaporated under reduced pressure to give an oil. The crude product was purified by column chromatography on silica gel using dichloromethane as eluant to afford the title compound (1.8 g).

$^1$H NMR (CDCl$_3$, 300 MHz) L 1.18 (t, 3H), 1.38 (m, 6H), 2.23 (q, 2H), 3.83 (q, 2H), 4.54 (d, 1H), 5.24 (m, 2H), 6.35 (m, 1H)

Preparation 4

Ethyl 2-oxo-3-(propionylamino)butanoate

Oxygen was bubbled through a cooled (−78° C.) solution of the alkene from Preparation 3 (1.0 g, 5.98 mmol) and pyridine (3.25 mL, 44.9 mmol) in dichloromethane (85 mL) for 2 minutes. Ozone was then bubbled through for 5 minutes and the solution then purged with oxygen, and placed under a nitrogen atmosphere. Dimethylsulphide (3.25 mL, 44.9 mmol) was added dropwise over 5 minutes, the solution stirred for an hour, and then allowed to warm to room temperature. The mixture was washed with water, dried (Na$_2$SO$_4$) and evaporated under reduced pressure to give an oil. The crude product was purified by column chromatography on silica gel using an elution gradient of dichloromethane:ether (100:0 to 50:50) to afford the title compound (395 mg).

$^1$H NMR (CDCl$_3$; 300 MHz) L 1.18 (t, 3H), 1.38 (m, 6H), 2.23 (q, 2H), 4.38 (q, 2H), 5.18 (m, 1H), 6.02 (m, 1H)

Preparation 5

2-Butoxynicotinic acid

2-Chloronicotinic acid (10.0 g, 63.5 mmol) was added to a solution of sodium (3 g, 130 mmol) in butanol (100 mL) at 80° C., and the resulting mixture heated under reflux for 4 hours. The reaction was allowed to cool, and partitioned between ethyl acetate and 2N hydrochloric acid (to give pH 3–4), and the layers separated. The organic phase was washed with brine, concentrated under reduced pressure, redissolved in ethyl acetate, dried (MgSO$_4$) and evaporated under reduced pressure, to give the desired product as a solid (11.9 g).

$^1$H NMR (DMSO d$_6$, 400 MHz) L 0.90 (t, 3H), 1.40 (m, 2H), 1.65 (m, 2H), 4.30 (t, 2H), 7.00 (m, 1H), 8.05 (d, 2H), 8.30 (d, 1H)

LRMS: m/z 196.3 (MH$^+$)

Preparation 6

2-Butoxy-5-iodonicotinic acid

A mixture of the acid from Preparation 5 (3.46 g, 17.7 mmol) and N-iodosuccinimide (6 g, 26.6 mmol) in trifluoroacetic acid:trifluoroacetic anhydride (4:1, 35 mL) was heated under reflux for 24 hours, with the exclusion of light. The cooled reaction mixture was concentrated under reduced pressure and the residue dissolved in ethyl acetate. This solution was then washed sequentially with water (twice), sodium thiosulphate solution (twice), 10% aqueous sodium citrate solution, 2N hydrochloric acid, and brine, then dried (MgSO$_4$), and evaporated under reduced pressure. The crude product was triturated with pentane to afford the title compound as a white solid, 3.86 g, 68%.

$^1$H NMR (CDCl$_3$, 300 MHz) L 1.00 (t, 3H), 1.50 (m, 2H), 1.85 (m, 2H), 4.60 (t, 2H), 8.50 (s, 1H), 8.70 (s, 1H), 10.50 (bs, 1H)

LRMS: m/z 322 (MH$^+$)

Preparation 7

2-Butoxy-5-iodonicotinonitrile

N,N-Dimethylformamide (3 drops) was added to an ice-cold suspension of the acid from Preparation 6 (2.25 g, 7.01 mmol) and oxalyl chloride (3.55 g, 28.0 mmol) in dichloromethane (20 mL), and the reaction stirred at room temperature for 4 hours. The mixture was concentrated under reduced pressure and the residue azeotroped with dichloromethane. The acid chloride was resuspended in dichloromethane (20 mL), cooled in an ice-bath, 0.88 ammonia (2 mL) was added and the solution stirred at room temperature for 30 minutes. The reaction mixture was diluted with dichloromethane, washed with water, 2N hydrochloric acid and brine, then dried (MgSO$_4$) and evaporated under reduced pressure to give a brown solid. A solution of trifluoroacetic anhydride (1.82 g, 8.67 mmol) in dioxan (2 mL) was added to an ice-cold solution of the intermediate amide (1.85 g, 5.78 mmol) and pyridine (1.14 g, 14.4 mmol) in dioxan (15 mL), and the reaction stirred at room temperature for 3 hours. The mixture was concentrated under reduced pressure and the residue partitioned between ethyl acetate and water, and the layers separated. The organic layer was washed with 2N hydrochloric acid (twice), saturated sodium bicarbonate solution, and brine, then dried (MgSO$_4$) and evaporated under reduced pressure. The crude product was purified by column chromatography on silica gel using an elution gradient of pentane:ethyl acetate (100:0 to 95:5) to give the title compound.

$^1$H NMR (CDCl$_3$, 300 MHz) L 0.98 (t, 3H), 1.50 (m, 2H), 1.80 (m, 2H), 4.40 (t, 2H), 8.08 (s, 1H), 8.50 (s, 1H)

LRMS: m/z 303.0 (MH$^+$)

Preparation 8

2-Butoxy-5-iodo-3-pyridinecarboximidamide formate

The nitrile from Preparation 7 (10 g, 33.1 mmol) was added to a freshly prepared solution of sodium (1.5 g, 65.2 mmol) in butanol (100 mL), and the reaction stirred at room temperature for 18 hours. Ammonium formate (17.4 g, 276 mmol) was added and the reaction heated to 50° C. for 2 hours, followed by a further 2 hours at 80° C. The cooled mixture was concentrated under reduced pressure and the residue triturated with ether. This solid was triturated with water, and then triturated several times with ether to afford the title compound (2.53 g), which was used without further purification.

$^1$H NMR (DMSOd$_6$, 400 Mhz) L 0.90 (t, 3H), 1.39 (m, 2H), 1.69 (m, 2H), 4.30 (t, 2H), 8.28 (s, 1H), 8.42 (s, 1H), 8.59 (s, 1H)

Preparation 9

2-(2-Butoxy-5-iodo-3-pyridinyl)-7-ethyl-5-methyl-4a,5-dihydroimidazo-[5,1-f][1,2,4]triazin-4(3H)-one Hydrazine hydrate (194 μL, 3.98 mmol) was added to a solution of the crude amidine from Preparation 8 (2.02 g, ca. 3.98 mmol) in ethanol (3.8 mL) and the solution stirred for 20 minutes. A solution of the ester from Preparation 4 (800 mg, 3.98 mmol) in ethanol (1 mL) was added and the reaction heated at 70° C. for 2 hours. The cooled mixture was concentrated under reduced pressure and the residue purified by column chromatography on silica gel using dichloromethane:ether (67:33) as eluant to give a yellow solid. This was triturated with ether to afford a yellow solid, 250 mg, (2:1 isomeric mixture of desired and undesired product). Phosphorous oxychloride (360 µL, 3.97 mmol) was added to a solution of this solid (243 mg, 0.516 mmol) in 1,2-dichloroethane (3 mL), and the reaction heated under reflux for 30 minutes. The cooled mixture was evaporated under reduced pressure and the residue partitioned between 2N sodium carbonate solution (5 mL) and ethyl acetate (5 mL), and the layers separated. The aqueous layer was extracted with ethyl acetate (2×5 mL) and the combined organic solutions dried ($MgSO_4$) and evaporated under reduced pressure to give a yellow solid. The crude product was purified by column chromatography on silica gel using dichloromethane:ether (91:9) as eluant to afford the title compound (130 mg).

$^1$H NMR ($CDCl_3$, 300 MHz) L 1.01 (t, 3H), 1.41 (t, 3H), 1.58 (m, 2H), 1.88 (m, 2H), 2.63 (s, 3H), 3.05 (q, 2H), 4.56 (t, 2H), 8.50 (d, 1H), 8.76 (d, 1H) 9.80 (s, 1H)

Preparation 10

2-(2-Butoxy-5-sulfanyl-3-pyridinyl)-7-ethyl-5-methyl-4a,5-dihydro-imidazo[5.1-f][1,2,4]triazin-4 (3H)-one A solution of triethylphosphine (9 mL, 1M in tetrahydrofuran; 9 mmol) was added to an ice-cold solution of nickel (II) chloride hexahydrate (1.0 g, 4.21 mmol) and the mixture stirred for 15 minutes. The resulting precipitate was filtered off and dried under vacuum, to give a red solid. A mixture of the iodide from Preparation 9 (135 mg, 0.30 mmol) and thiourea (34 mg, 0.45 mmol) in N,N-dimethylformamide (1 mL) was heated to 70° C., then the previously prepared red solid (22 mg), and sodium cyanoborohydride (5.6 mg, 0.09 mmol) were added, and the mixture stirred at 70° C. for 2½ hours, then stirred at room temperature for 18 hours. Calcium oxide (25 mg, 0.45 mmol), followed by N,N-dimethylformamide (1 mL) were added, and the mixture stirred for a further 90 minutes. The reaction was cooled in an ice-bath, quenched by the addition of hydrochloric acid (2N), the mixture partitioned between ethyl acetate (15 mL) and water (15 mL), then basified to pH using sodium bicarbonate solution. The phases were separated, the aqueous layer extracted with ethyl acetate (5×20 mL), the combined organic solutions dried ($MgSO_4$) and evaporated under reduced pressure. The crude product was purified by column chromatography on silica gel using dichloromethane:methanol (97:3) as eluant to give the title compound (47 mg).

$^1$H NMR ($CDCl_3$, 300 Mhz) L 1.01 (t, 3H), 1.39 (t, 3H), 1.56 (m, 2H), 1.87 (m, 2H), 2.62 (s, 3H), 3.01 (q, 2H), 4.58 (t, 2H), 8.38 (d, 1H), 8.68 (d, 1H), 9.82 (s, 1H)

LRMS: m/z 360.1 ($MH^+$)

EXAMPLE 1

2-{2-Butoxy-5-[(4-ethyl-1-piperazinyl)sulfonyl]-3-pyridinyl}-7-ethyl-5-methyl-4a,5-dihydroimidazo[5,1-f][1,2,4]triazin-4(3H)-one A solution of the thiol from Preparation 10 (47 mg, 0.13 mmol) and potassium nitrate (33 mg, 0.33 mmol) in acetonitrile (1.2 mL) was cooled in an ice-bath, thionyl chloride (26.3 µL, 0.33 mmol) was added, and the solution stirred at 0° C. for an hour. The reaction was concentrated under reduced pressure and the residue partitioned between sodium bicarbonate solution (8 mL) and dichloromethane (10 mL), and the layers separated. The aqueous layer was extracted with dichloromethane (5 mL), the combined organic solutions dried ($MgSO_4$) and concentrated under reduced pressure to a volume of 5 mL. This solution was cooled to 0° C., N-ethyl piperazine (83 µL, 0.65 mmol) added, and the solution stirred for 20 minutes. Sodium bicarbonate solution (15 mL) was added and the mixture extracted with ethyl acetate (2×20 mL). The combined organic extracts were dried ($MgSO_4$) and evaporated under reduced pressure to give a gum. The crude product was purified by column chromatography on silica gel using dichloromethane:methanol (97:3) as eluant to give the title compound (15 mg).

$^1$H NMR ($CDCl_3$, 300 Mhz) L 1.02 (m, 6H), 1.40 (t, 3H), 1.58 (m, 2H), 1.92 (m, 2H), 2.42 (q, 2H), 2.58 (m, 4H), 2.64 (s, 3H), 3.02 (q, 2H), 3.14 (m, 4H), 4.62 (t, 2fH), 8.65 (d, 1H), 8.77 (d, 1H), 9.65 (bs, 1H)

LRMS: m/z 504.6 ($MH^+$)

Biological Activity

Compounds of the invention were found to have in vitro activities as inhibitors of cGMP PDE5 with $IC_{50}$ values of less than about 100 nM.

Abbreviations

The following abbreviations may be used herein:

| | | |
|---|---|---|
| Ac | = | acetyl |
| DCM | = | dichloromethane |
| DMF | = | N,N-dimethylformamide |
| DMSO | = | dimethylsulfoxide |
| Et | = | ethyl |
| EtOAc | = | ethyl acetate |
| HPLC | = | high performance liquid chromatography |
| IPA | = | iso-propyl alcohol (propan-2-ol) |
| Me | = | methyl |
| MeCN | = | acetonitrile |
| MeOH | = | methanol |
| OAc | = | acetate |
| THF | = | tetrahydrofuran |

What is claimed is:
1. A compound of formula I,

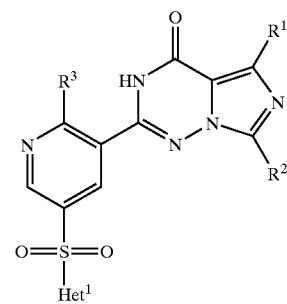

wherein
$R^1$ and $R^2$ independently represent phenyl (optionally substituted by one or more substituents selected from halo, —CN, —$CF_3$, —$OCF_3$, $C_{1-4}$ alkoxy or $C_{1-4}$ alkyl (which latter two groups are optionally substituted by $C_{1-4}$ haloalkyl or $C_{1-4}$ haloalkoxy)) or $C_{1-6}$ alkyl optionally interrupted by —O—, —S— and/or —N($R^4$)— and/or optionally substituted and/or terminated by $Het^2$, a N-linked heterocyclic group (selected from piperidinyl and morpholinyl) or phenyl (which latter group is optionally substituted by one or more substituents selected from halo, —CN, —$CF_3$, —$OCF_3$, $C_{1-4}$ alkoxy or $C_{1-4}$ alkyl (which latter two groups are optionally substituted by $C_{1-4}$ haloalkyl or $C_{1-4}$ haloalkoxy));

$R^4$ represents H or $C_{1-4}$ alkyl;

$R^3$ represents $OR^5$ or $N(R^6)R^7$;

$R^5$ represents $C_{3-6}$ cycloalkyl, —($C_{1-4}$ alkylene)-1-piperidinyl, tetrahydrofuranyl, tetrahydropyranyl or $C_{1-6}$ alkyl, which latter group is optionally substituted and/or terminated by one or two substituents selected from $C_{3-5}$ cycloalkyl, —$OR^8$, —$N(R^6)R^7$, phenyl, furanyl and pyridinyl, and which $C_{1-6}$ alkyl group is optionally terminated by a $C_{1-4}$ haloalkyl group;

$R^6$ and $R^7$ independently represent, at each occurrence, H, $C_{1-4}$ alkyl (optionally substituted by $C_{3-5}$ cycloalkyl or $C_{1-4}$ alkoxy), or $R^6$ and $R^7$, together with the nitrogen atom to which they are attached, form an azetidinyl, pyrrolidinyl, piperidinyl or morpholinyl group;

$R^8$ represents H, $C_{1-4}$ alkyl (which $C_{1-4}$ alkyl group is optionally terminated by a $C_{1-4}$ haloalkyl group) or benzyl;

$Het^1$ represents a 4-$R^9$-1-piperazinyl group optionally substituted with one or two $C_{1-4}$ alkyl groups and optionally in the form of its 4-N-oxide;

$R^9$ represents H, pyridinyl, pyrimidinyl, $C_{3-6}$ alkenyl or $C_{1-4}$ alkyl optionally substituted by one or two substituents selected from —OH, —$N(R^6)R^7$, —C(O)N($R^6)R^7$, benzodioxolyl, benzodioxanyl or phenyl (which latter group is optionally substituted by $C_{1-4}$ alkoxy);

$Het^2$ represents a C-linked 6-membered heterocyclic group containing one or two nitrogen atoms, optionally in the form of its mono-N-oxide, or a C-linked 5-membered heterocyclic group containing two or three nitrogen atoms, wherein either of said heterocyclic groups is optionally substituted with $C_{1-4}$ alkyl, $C_{1-4}$ alkoxy or $N(H)R^{10}$; and $R^{10}$ represents H, $C_{1-4}$ alkyl or $C_{1-4}$ alkanoyl;

or a pharmaceutically, or a veterinarily, acceptable derivative thereof.

2. A compound as claimed in claim 1, wherein $R^1$ and $R^2$ independently represent optionally substituted phenyl or $C_{1-4}$ alkyl optionally substituted and/or terminated by $Het^2$ or optionally substituted phenyl.

3. A compound as claimed in claim 1, wherein $R^3$ represents $OR^5$.

4. A compound as claimed in claim 1, wherein $R^5$ represents $C_{1-5}$ alkyl optionally substituted and/or terminated by $C_{1-2}$ alkoxy.

5. A compound as claimed in claim 1, wherein $Het^1$ represents a 4-$R^9$-1-piperazinyl group.

6. A compound as claimed in claim 1, wherein $R^9$ represents $C_{1-4}$ alkyl.

7. A compound as claimed in claim 1, wherein $Het^2$ represents an optionally substituted C-linked 6-membered heterocyclic group containing two nitrogen atoms.

8. A formulation comprising a compound as defined in claim 1 in admixture with a pharmaceutically or veterinarily acceptable adjuvant, diluent or carrier.

9. A formulation as claimed in claim 8, which is a pharmaceutical formulation.

10. A formulation as claimed in claim 8, which is a veterinary formulation.

11. A method of treating or preventing a medical condition for which inhibition of cGMP PDE5 is desired or required, which comprises administering a therapeutically effective amount of a compound as defined in claim 1 to a patient in need of such treatment.

12. A method as claimed in claim 11, wherein the condition is male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD).

13. A process for the preparation of a compound of formula I, as defined in claim 1, which comprises:

(a) reaction of a compound of formula II,

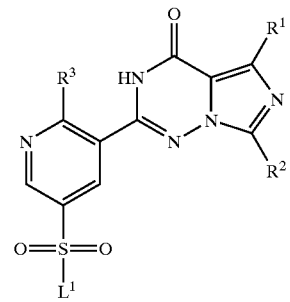

wherein $L^1$ represents a leaving group, and $R^1$, $R^2$ and $R^3$ are as defined in claim 1, with a compound of formula III, $Het^1$—H  III wherein $Het^1$ is as defined in claim 1, provided that the 1-N atom of the piperazine is attached to the H-atom;

(b) cyclisation of a compound of formula XXI,

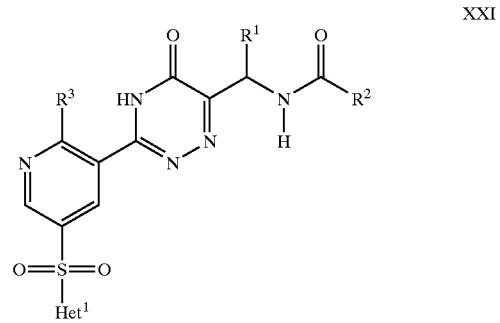

wherein $R^1$, $R^2$, $R^3$ and $Het^1$ are as defined in claim 1;

(c) conversion, removal or introduction of a substituent on a phenyl, or a Het ($Het^1$, $Het^2$) group in, or on the pyridinyl, or imidazotriazinone, unit of, a compound of formula I;

(d) for compounds of formula I in which $R^3$ represents $OR^5$, conversion of one $OR^5$ group to another by alkoxide exchange;

(e) for compounds of formula I in which $Het^1$ represents a 4-$R^9$-1-piperazinyl group in which $R^9$ represents optionally substituted $C_{1-4}$ alkyl, alkylation of a corresponding compound of formula I in which $R^9$ represents H; or (f) deprotection of a protected derivative of a compound of formula I.

14. A compound of formula II, as defined in claim 13.

15. A compound of formula XXI, as defined in claim 13.

16. A method as claimed in claim 11, wherein the condition is male erectile dysfunction (MED).

* * * * *